United States Patent [19]

Wagner et al.

[11] Patent Number: 4,940,669
[45] Date of Patent: Jul. 10, 1990

[54] SAC INCLUDING A DETECTABLE METAL MARKER AND USE THEREOF IN AN ASSAY

[75] Inventors: Daniel B. Wagner, Raleigh; Glenn P. Vonk, Fuquay-Varina, both of N.C.

[73] Assignee: Becton Dickinson and Company, Franklin Lakes, N.J.

[21] Appl. No.: 49,971

[22] Filed: May 15, 1987

[51] Int. Cl.$^5$ ............... G01N 33/566; G01N 33/543; G01N 33/544; G01N 33/532
[52] U.S. Cl. .................... 436/501; 436/518; 436/519; 436/528; 436/536; 436/544; 436/546; 436/800; 436/821; 436/829; 514/78
[58] Field of Search ............... 436/501, 536, 537, 800, 436/821, 829, 518, 519, 528, 544, 546; 514/78

[56] References Cited

U.S. PATENT DOCUMENTS

| | | | |
|---|---|---|---|
| 4,310,506 | 1/1982 | Baldeschweiler et al. | 424/9 X |
| 4,483,929 | 11/1984 | Szoka | 436/533 |
| 4,707,453 | 11/1987 | Wagner et al. | 436/528 X |
| 4,743,560 | 5/1988 | Campbell et al. | 436/528 X |

FOREIGN PATENT DOCUMENTS 1258172  11/1986  Japan ................... 436/546

*Primary Examiner*—Jack Spiegel
*Attorney, Agent, or Firm*—Elliot M. Olstein; John G. Gilfillan; John N. Bain

[57] ABSTRACT

A sac, in particular a vesicle, having a detectable metal, in particular a rear earth metal, encapsulated therein. The sac may be sensitized with a ligand and used in an assay. The vesicle is stored and/or used in an aqueous solution which includes the rare earth metal to increase the concentration of metal in the sac.

17 Claims, No Drawings

SAC INCLUDING A DETECTABLE METAL MARKER AND USE THEREOF IN AN ASSAY

This invention relates to sacs including a detectable marker, and the use thereof in an assay for an analyte. This invention further relates to sacs including a detectable marker which are sensitized with a ligand, and the use thereof in an assay for an analyte.

Sacs, and in particular, lipid vesicles, which include a detectable marker therein have been employed in assays for a ligand (analyte). In a representative assay, a ligand to be determined (analyte) and tracer comprised of a sac containing a detectable marker sensitized with the analyte or appropriate analog thereof compete for a limited number of binding sites on a binder for the analyte. The amount of tracer which becomes bound to the binder is inversely proportional to the amount of analyte in the sample. After separating bound and free tracer components, the amount of the bound and/or free tracer is ascertained by determining the detectable marker in the bound and/or free tracer portion of the sample, which provides a measure of analyte in the sample.

In accordance with one aspect of the present invention, there is provided a sac which includes a chelated detectable metal ion or atom encapsulated therein, which metal atom or ion is fluorescent when complexed with an activator.

Rare earth metals of both the actinide and lanthanide series are preferred. As representative example, there may be mentioned terbium, prosium, europium, samarium, and neodimium.

A rare earth metal is preferred in that such rare earth metal may be employed as a detectable marker in an assay which relies on fluorescence, and in particular, a time-delay fluorescent assay.

In accordance with another aspect of the present invention, a sac including a detectable metal as hereinabove described is sensitized with a ligand, which is either an antigen, hapten or antibody.

In accordance with yet a further aspect of the present invention, a sac including a detectable metal as hereinabove described, is employed in an assay for an analyte. The sac including the detectable metal may be employed with or without sensitization with a ligand, depending upon the particular assay procedure.

In accordance with a further aspect of the present invention, there is provided a composition of a vesicle in an aqueous solution wherein the vesicle has encapsulated therein a chelated rare earth metal and wherein the aqueous solution includes the rare earth metal in chelated and/or unchelated form, preferably unchelated form. Applicant has found that the concentration of rare earth metal within the vesicle may be increased by including rare earth metal in the aqueous solution in which the vesicle is stored and/or used in an assay. In effect by maintaining a concentration of rare earth metal in the solution exterior to the sac, it is possible to increase and/or maximize the concentration of rare earth metal inside of the sac.

In accordance with a preferred aspect, the aqueous solution includes the rare earth metal in an amount whereby the rare earth metal is encapsulated in the sac in a concentration of at least 5 millimolar, preferably at least 10 millimolar. In most cases, the rare earth metal is encapsulated in a concentration of at least 15 millimolar or 20 millimolar.

The sacs, which include a detectable metal in the interior thereof, may be any one of the wide variety of sacs which are generally known in the art, including polymer microcapsules (for example, those made by coascervation or interfacial polymerization), or vesicles which may be prepared from a wide variety of materials, preferably prepared from lipids. When the vesicle includes a lipid, it is often referred to as a liposome; however, as known in the art, vesicles can be produced from amphiphilic components which are not lipids. As known in the art, liposomes can be prepared from a wide variety of lipids, including phospholipids, glycolipids, steroids, relatively long change alkyl esters, e.g., alkyl phosphates, fatty acid esters, e.g., lecithin, fatty amines and the like. A mixture of fatty materials may be employed such as a combination of neutral steroid, a charged amphiphile and a phospholipid. As illustrative examples of phospholipids there may be mentioned sphingomyelin, dipalmitoyl, lecithin, and the like. As representative steroids, there may be mentioned cholesterol, cholestanol, lanosterol, and the like. As representative examples of charged amphiphilic compounds, which generally contain from 12 to 30 carbon atoms, there may be mentioned mono or dialkyl phosphate ester, quaternary ammonium salts, or an alkylamine; e.g., dicetyl phosphate, distearyl amine, dihexadecyl amine, dilauryl phosphate, dioctadecyl sulfonate, didodecyl dioctylammonium formide, and the like.

Vesicles may be prepared by any one of a wide variety of procedures. Thus, for example, a liposome may be prepared by a reverse emulsion technique, as described in U.S. Pat. No. 4,235,871, wherein there is provided a water-in-oil emulsion containing the materials for forming the vesicle (generally phospholipids), as well as the chelated detectable metal to be encapsulated in the vesicle, followed by evaporation of the solvent to produce a gel-like mixture which is converted to a vesicle by either agitation or addition of the gel-like mixture to water.

Another procedure for producing a sac containing an encapsulated material is described in U.S. patent application Ser. No. 650,200 filed on Sept. 13, 1984, and such procedure may also be employed for producing a sac containing a chelated detectable metal in accordance with the invention.

Further procedures for producing sacs containing encapsulated markers are also disclosed in U.S. Pat. No. 4,343,826 and P.C.T. International Publication No. WO 80/01515 and such procedures are applicable to the present invention.

Polymer microcapsules are produced by procedures known in the art, except that the solution in which the microcapsules are formed also includes a chelated detectable metal whereby the interior of the polymer microcapsule includes the detectable metal. The preparation of such microcapsules is disclosed, for example, in *Microencapsulation Process and Applications*, edited by Jan E. Vandegger (Plenum Press 1974).

As hereinabove indicated, the sacs which include a detectable metal of the type hereinabove described may be sensitized with a ligand. The ligand is generally either an antigen, antibody or hapten and when sensitized, such sacs may be employed in an assay for an analyte. For example, the sacs may be sensitized with a ligand by coupling the ligand to the sacs by a variety of procedures, including covalent coupling, derivatization, activation and the like.

The sacs may be coupled to the ligand by the use of an appropriate coupling or spacer compound (one that does not destroy the immunoreactivity of the ligand). As known in the art, the coupling compound has two reactive functional groups, one of which functional groups is capable of reacting or being linked to a functional group of the ligand portion of the tracer, and the other of which is capable of reacting or being linked to a functional group on the sacs. For example, the spacer or coupling compound, which includes at least two reactive substituent groups, may contain either a carboxyl, isocyanate, isothiocyanate, amino, thiol, hydroxy, sulfonyl, carbonyl, etc., substituent group, which, as should be apparent, is dependent upon the functional group present in the ligand and sacs which are to be coupled to each other.

Alternatively, the sacs may be coupled directly to the ligand. Thus, for example, if the ligand portion of the tracer has an amino substituent group, and the sac portion of the tracer has a carbonyl or carboxyl substituent group, then the ligand and sacs may be directly conjugated to each other by procedures known in the art; for example, an active ester technique.

The sacs may be sensitized with the ligand by either coupling the ligand to one of the materials to be used in forming the sacs or by coupling the ligand to the sacs after they are formed. Such procedures are generally known in the art, and no further details in this respect are deemed necessary for a complete understanding of the invention.

The detectable metal is encapsulated in the sac in a chelated or complexed form. Any one of a wide variety of chelating agents may be employed for such purpose, and as representative examples of such chelating agents, there may be mentioned aminocarboxylic acids, iminocarboxylic acids, ethers, thiols, phenols, glycols and alcohols or polyamines, ethylenediaminetetracetates, diethylenetriaminepenta- or tetracetates, polyethers, polythiols, cryptands, polyetherphenolates, polyether thiols, ethers of thioglycols or alcohols, polyaminephenols, all either acyclic, macrocyclic, cyclic, macrobicyclic or polycyclic, or other similar ligands which produce highly stable metal chelates or cryptates.

The selection of a particular chelating agent will depend upon the metal to be chelated.

The chelating agents which are particularly preferred are aminocarboxylic acids; and in particular, ethylenediaminetetraacetic acid (EDTA) and diethylenetriaminepentaacetic acid (DTPA).

It is to be understood that the chelating compound may be one which also functions as an activator, as hereinafter described, whereby the metal is present in the sac as a fluorescent complex.

As hereinabove indicated, the sac containing a detectable metal of the types hereinabove described may be employed in an assay for determining an analyte in a sample. The sac may or may not be derivatized with a ligand.

In the case where the sac is derivatized with a ligand for use in determining an analyte in a sample, the derivatized sac is generally referred to in the art as a "tracer". The ligand which is employed for derivatizing the sac is dependent upon the analyte to be determined. Thus, for example, if the assay is a competitive immunoassay for determining an antigen or hapten, the ligand employed in producing the tracer is either the analyte or appropriate analog thereof. (The term "appropriate analog" means that the analog of the analyte is bound by the binder for the analyte).

If the assay is a "sandwich" type of immunoassay, then the ligand employed in producing the tracer would be a ligand bound by the analyte to be assayed; for example, an antibody elicited in response to the antibody or antigen to be assayed. Alternatively, the ligand may be anti-IgG.

Thus, as should be apparent, the ligand which is employed for producing the tracer may be either an antigen, a hapten or an antibody.

The binder which is used in the assay is also dependent upon the analyte. Thus, for example, if the analyte is an antigen or hapten, the binder may be an antibody or a naturally occurring substance which is specific for the analyte. If the analyte is an antibody, the binder may be either an antibody, an antigen or naturally occurring substance which is specific for the analyte.

The binder which is used in the assay may be employed in supported or unsupported form. If supported, the binder may be supported on a wide variety of materials which are generally known to be suitable as supports for a binder in an assay. As representative examples of such materials, there may be mentioned polymers, glass particles, bacterial cells, etc. The solid support may be in a wide variety of forms, including sheet form, tube form, as a card or test strip, etc.

Thus, in accordance with another aspect of the present invention, there is provided an assay for an analyte in a sample which employs a binder and tracer wherein the binder binds at least the analyte, and the tracer is bound by one of the analyte and binder to provide in the assay free and bound tracer fractions. In the assay, a sac including a detectable metal of the type hereinabove described is the source of the detectable marker in the assay.

In accordance with a preferred procedure, the tracer is formed by use of a vesicle containing a chelated rare earth metal, such as europium. As known in the art, europium may be detected by fluorescence.

The fluorescent rare earth metal, and in particular, europium, as generally known in the art, is fluorescent when activated with a suitable activating compound, such as a beta-diketone or a dihydroxy compound, such as sulfosalicylic acid.

The most widely used B-diketones are benzoylacetone (BA), dibenzoylmethane (DBM), thenoyltrifluoracetone (TTA), benzoyltrifluoroacetone (BTA), 1- and 2- naphthoyltrifluoroacetone (1-/2-NTA), acetylacetone (AcA), trifluoroacetylacetone (TFAcA), and hexafluoroacetylacetone (HFAcA). In addition, to B-diketones the lasering properties of different salicylate chelates have previously been investigated and different methods for fluorometric determination of lanthanide ions (Eu, Tb, Sm, Dy) has been developed using these compounds and other ligands, such as terbium with dipicolinic acid (DPA) and with EDTA and sulpho salicyl acid (SSA). Under favorable conditions the quant yield of these chelates can be very high and come close to 100 percent.

The beta-diketone may be provided as a chelate, which chelates the rare earth metal. Use of beta-diketone or other activating compound in this manner is disclosed in U.S. Pat. No. 4,374,120.

Activating compounds are also described in European application No. 0-171-978, and in PCT Application WO84/03698.

In accordance with a preferred embodiment, the rare earth metal is caused to be fluorescent by the use of a suitable activating compound, such as a beta-diketone, after separating the rare earth metal from the chelate.

Thus, for example, a lanthanide, such as europium, may be separated from the chelating agent by use of a suitable detergent, such as Triton-X-100 at a low pH value. After separation of the lanthanide, the fluorescence may be amplified by the use of a suitable activating material, such as a beta-diketone. In addition, in order to improve the fluorescence, a Lewis base may be added. Such bases are known, and are generally N-heterocyclic compounds such as o-phenanthroline, phosphines, and phosphine oxides.

Thus, in accordance with a preferred embodiment, the assay is accomplished by employing a fluorescent rare earth metal (a rare earth metal which is fluorescent when activated) as the detectable marker, and fluorescence is read by procedures known in the art, with the preferred method being removal of the europium from the chelate, and activation thereof with a beta-diketone, and preferably also a Lewis base.

The assay may be preferably effected by a time delay fluorescent method, however, in some cases, it may be possible to determine fluorescence without a time delay, although a time delay is preferred in that it eliminates background fluorescence. The principles behind a time delay fluorescent assay are known in the art, and such principles are equally applicable to a time delay fluorescent assay in accordance with the present invention wherein the rare earth metal is encapsulated in the sac.

Thus for example, in such an assay, after separating bound and free components, the europium is removed from the liposome by use of a detergent, and by addition of a beta-diketone and a Lewis base. The europium is then excited, for example, at 340 nm, and the beta-diketone absorbs energy and transfers the energy to the europium which fluoresces at 614 nm. Fluorescence may be determined in suitable instrumentation available in the art, after a suitable period for permitting decay of background fluorescence, as generally practiced in the art.

In accordance with a representative assay, a sample containing or suspected of containing the analyte is incubated with a tracer, which is the analyte or appropriate analog thereof coupled to sacs including a chelated detectable metal, in particular, chelated europium, and a binder specific for both the analyte and tracer with the binder preferably being supported on a solid support. The incubation results in competition between the tracer and analyte for binding sites on the binder, with the amount of tracer which is bound to the binder being inversely proportional to the amount of analyte in the sample.

The incubation is effected under conditions which prevent premature rupturing of the scas. This portion of the assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs. In general, the buffer provides a pH in the other of from 5 to 9.

After incubation, the tubes are aspirated, whereby a tube includes only the bound tracer component. Subsequently, a solution containing a beta-diketone, a Lewis base, and a detergent, is added to the tube. The detergent serves the dual purpose of lysing the vesicle of the bound tracer and removing the europium from the chelating agent.

After a time period which permits decay of background fluorescence, fluorescence of the europium is determined on suitable instrumentation by excitation at 340 nm, and reading emission at 614. The amount of tracer bound to the tube is inversely proportional to the amount of hapten in the sample, and the quantity may be determined by the use of a suitable standard curve prepared from standards having known amounts of hapten.

Similarly, a tracer in accordance with the present invention may be employed in a "sandwich" type of assay, in which case, the tracer is formed from a vesicle including chelated europium and derivatized with a ligand which is bound by the analyte. The assay may be conducted in a tube coated with a binder specific for the analyte, and fluorescence determined as hereinabove described. In this type of assay, the amount of tracer which is bound to the tube through the analyte and coated binder is directly proportional to the amount of analyte in the sample.

As a further alternative, in a sandwich assay the tracer may be a vesicle derivatized with anti-IgG, in which case the tracer is not bound directly to the analyte; i.e. in the assay, analyte is bound to both a binder specific for the analyte supported on a solid support and to an antibody specific for the analyte, with the tracer identifying the antibody in the bound portion.

In some cases, it may be possible to employ a sac including a detectable metal of the type hereinabove described in an assay for an analyte, without derivatizing the sac. Thus, for example, in one type of assay, an analyte in a sample is incubated with a binder for the analyte supported on a solid support, and a tracer which is the analyte or appropriate analog thereof derivatized with an enzyme lysing agent. The tracer and analyte compete for binding sites on the binder, and after separating bound and free portions thereof, the bound and/or free portions may be contacted with a vesicle including a detectable metal of the type hereinabove described, with the rate of release of marker from the sac, and/or amount of marker released from the sac being dependent upon the amount of tracer in the bound and/or free fraction. As generally practiced in the art, a standard curve may be prepared by repeating the assay with known quantities of analyte.

Thus, as should be apparent, the sac which includes a detectable metal of the type hereinabove described may be employed in a variety of assays, and such sac may be employed in the assay with or without derivatization with a ligand.

The assays may be effected in wide variety of samples. In most cases, the assay is effected in a sample of body fluid, such as, serum, urine, sputum, etc.

The assay may be employed for determining a wide variety of analytes. As representative examples of the types of analytes, there may be mentioned: drugs, including therapeutic drugs and drugs of abuse; hormones, vitamins; proteins, including antibodies of all classes; peptides; steroids; bacteria; fungi; viruses; parasites; components or products of bacteria, fungi, viruses or parasites; allergens of all types; products or components of normal or malignant cells; etc. As particular examples, there may be mentioned $T_4$; $T_3$; digoxin; hCG; TSH, insulin, hCG theophylline; antibiotics, such as gentamicin and tobramycin; anticonvulsants, such as phenobarbital, carbamezapine, valpric acid, antiarrythmics, such as lidocaine, quinidine; etc.

Thus, in accordance with an embodiment of the present invention, there is provided a sac, and in particular, a vesicle or liposome, which includes a detectable metal and such sac may or may not be derivatized with a ligand; in particular, an antigen, hapten or antibody. The sac when derivatized with a ligand is particularly useful as a tracer in an assay for an analyte in a sample wherein the analyte is measured either qualitatively (presence or absence), or quantitatively (amount of analyte).

In accordance with the present invention, there may be provided a reagent kit or package which includes in appropriate containers a sac including a detectable metal, as hereinabove described, which is derivatized with a ligand and which kit further includes a binder specific for the analyte, which is preferably supported on a solid support. The kit may also include appropriate buffers, standards, chemicals for activating, chemicals for lysing a vesicle, etc.

The present invention will be further described with respect to the following example; however, the scope of the invention is not to be limited thereby:

EXAMPLE 1

1. Liposome Preparation

A solution of phosphatidylcholine (94 mg, 111 umol), phosphatidylglycerol (10.3 mg, 13.5 umol), cholesterol (50.9 mg, 131.5 umol) and phosphatidyl-ethanolamine-MC (3.75 mg., 3.93 umol) in chloroform was evaporated in a 250 mL flask such that the lipid mixture formed a thin film on the flask wall.

In a separate flask was prepared a solution of diethylenetriaminepentacetic acid (DTPA, 787 mg, 0.002 mol) and europium nitrate hexahydrate (806 mg, 0.018 mol) in deionized water (40 mL) at pH 7 (5N aqueous sodium hydroxide). The europium-DTPA solution was filtered through a 0.2 micron polycarbonate membrane. The osmolality of the solution was about 325 mOSM.

A portion of the above europium-DPTA solution (20 mL) was added to the dry lipids and the resulting mixture warmed at 50–60 C. for 5 min. A brief sonication at low power displaced any remaining lipids from the flask wall. The mixture was then extruded through polycarbonate membranes (5, 2×0.4, 2×0.2 micron) and washed by centrifugation three times at 75,000×g with wash buffer (90 mL per wash, 50 mM Tris, 50 mM sodium acetate, 50 mM sodium chloride, $10^{-7}$M europium nitrate, pH 7.0). After the final wash the pellet was resuspended in 10 ml of the same buffer.

2. Antibody Conjugation

During liposome centrifugation monoclonal anti-HCG (2.0 mg, 1.0 mg/mL in 50 mM sodium acetate, 50 mM sodium phosphate, 100 mM sodium chloride, pH 6.5) was reduced with Dithiothreitol (1M in the same buffer as antibody, 50 uL/mg antibody) and purified after 1 h by chromatography on Sephadex G-25, eluting with coupling buffer (50 mM tris, 50 mM sodium acetate, 50 mM sodium chloride, pH 8.0). The purified reduced antibody was then added (4 mL) to half of the above liposome preparation and allowed to stand overnight at room temperature in the dark.

The liposomes were then washed twice by centrifugation (75,000×g) in coupling buffer (45 mL) and after the final centrifugation resuspended in storage buffer (20 mL, 20 mM Tris, 20 g/L glycerol, 0.5 mL/L DMSO, 0.2 g/L sodium azide, $10^{-7}$ molar europium nitrate, pH 7.4, adjustment of mOSM to 350 with sodium chloride, and readjustment of pH to 7.4).

3. Assay Procedure

Microtitere strips (Titretek) were coated with monoclonal anti-HCG in a concentration of 1.76 ug/mL in bicarbonate coating buffer (sodium carbonate 1.59 g/L, sodium bicarbonate 2.93 g/L, thimerosal 0.1 g/L). After incubation overnight at 40444 C., the strips were washed with coating buffer (3×) and blocked with a solution of 2% BSA in coating buffer at pH 9.6 (NaOH) under the same conditions. The strips were washed in wash buffer (6×, 50 nM HEPES, NaCl 9 g/L, BSA 2%, pH 7.7) and stored humid at 4C.

The analyte was then diluted in the wash buffer to appropriate concentrations and distributed into the coated microtitere strips. These strips were then incubated from 3 to 16 hours at which time the strips were washed with wash buffer (6×) and incubated with liposomes diluted 1/500 times in liposome assay buffer (200 uL, 50 nM HEPES, NaCl 9 g/L, BSA 2%, Glycerol 1% DTPA 10-4M, $10^{-7}$M europium nitrate, pH 7.7). The number of counts added is approximately 1.6×108. After 0.5 h the strips were washed 11 times with wash buffer. Enhancement solution (200 uL., LKB Wallac 1244-104) was added and the strips read after 10 minutes on the Arcus 1230 fluorometer.

The assay sensitivity in serum is 0.2 m IU/ml and in buffer the sensitivity if 0.025 m IU/ml.

In general, the sensitivity of hcG assays is 2 m IU/ml.

EXAMPLE 2

Thyroid Stimulating Hormone (TSH) Binding Assay

The liposomes for this assay were prepared according to the procedure of example 1, up to antibody conjugation. At this point, monoclonal anti-TSH (BD clone 6, 45-108, batch D009-007) was reduced with DTT and purified by gel filtration as before. The antibody concentration was determined (OD 1.4=1 mg/mL) and 380 ug reduced antibody added to half of a liposome preparation as described above. The liposomes were allowed to stand overnight at ambient temperature in the dark, then washed free of antibody by centrifugation as described above except that the wash buffer was changed slightly by the addition of sodium acetate (20 mL, 20 mM tris, 50 mM sodium acetate, 20 g/L glycerol, 0.5 mL/L DMSO, 0.2 g/L sodium azide, $10^{-7}$ molar europium nitrate, pH 7.4, mOSM 314). The liposomes were stored in the wash buffer (20 mL).

Microtitre strips (Titretek) were coated with commercially obtained monoclonal anti-TSH (Medix, T-790-06) as a solution (1 ug/mL) in bicarbonate coating buffer (sodium carbonate 1.59 g/L, sodium bicarbonate 2.93 g/L, thimerosal 0.1 g/L, pH 9.6). Aliquots (200 uL) were distributed to each well and incubated at 4C. overnight. The wells were washed with PBS (3×), blocked overnight with tris-BSA buffer (50 mM tris, sodium chloride 9 g/L, BSA 0.5%, pH 7.7), washed with N-2-Hydroxyethylpiperazine-N'-2-ethane sulfonic acid (HEPES) wash buffer (3×) and stored humid at 4C.

The assay was run according to the following procedure. Microtitre strips were washed with HEPES wash buffer (3×). TSH serum standards 50 uL/well, were placed in each well and a solution of liposomes (10 uL) in HEPES assay buffer containing $10^{-7}$M europium nitrate (10 mL) added (150 uL/well). The strips were covered with acetate film, shaken for 15 min, and washed with HEPES wash buffer (6×). Enchancement solution comprised of Triton X-100, 2 naphthoyltrifluoroacetone, and Tri-n-octylphosphine oxide, buffered to a pH of 3.2 (1244-104 Enhancement solution sold by LKB Wallac) was added, and the signal read after 10 minutes on an Arcus 1230 time resolved spectrofluorometer.

The standard curve extends from 54 uIU/mL to 0.25 uIU/mL. Correlation of the expected dose with the actual dose gave a correlation coefficient of 0.99 (slope 0.979, intercept 0.299).

EXAMPLE 3

Herpes Simplex Virus Type 1 Binding Assay

The liposomes for this assay were prepared according to the procedure in example 1 up to antibody conjugation. At this point monoclonal anti-herpes simplex virus antibody (Becton Dickinson, clone 67) was reduced with DTT and purified on sephadex G-25. The antibody concentration was determined and the reduced antibody (2 mg) added to the standard 1×liposome preparation. The liposomes were allowed to stand overnight at room temperature in the dark, then washed free of unreacted antibody by centrifugation, and stored in the same manner of example 1.

Microtitre strips (Titretek) were coated with a solution (200 uL/well) of herpes simplex virus (1 ug/L) in bicarbonate coating buffer (sodium carbonate 1.59 g/L, sodium bicarbonate 2.93 g/L, thimerosal 0.1 g/L, pH 9.6) overnight at 4 C. The wells were washed with PBS three times and blocked with tris-BSA buffer (50 mM tris, sodium chloride 9 g/L, BSA 0.5% sodium azide 0.1%, pH 7.7, 300 uL/well) overnight at 4 C. The wells were washed with HEPES wash buffer and stored humid at 4 C.

The assay was run according to the following procedure. Standards were prepared from Vero cell lysates known to contain 67 ug of herpes antigen/mg of protein in the lysate by dilution in HEPES liposome wash buffer. A blank was prepared from uninfected Vero cell lysate (324 ng/mL). Standards were distributed to wells (100 uL/well) followed by addition of diluted liposomes (5 uL liposome preparation/10 mL HEPES liposome wash buffer, containing $10^{-7}$ europium nitrate, 100 uL per well). The wells were covered with acetate film and shaken for 1 h at room temperature. The strips were washed with HEPES wash buffer (6×), enhancement solution added (200 uL), and read after 30 min. on an Arcus 1230 time-resolved fluorimeter.

The standard curve extends from over 300 to ca. 7 ng Vero lysate/mL. The detection limit was ca. 10 ng/mL. This corresponds to detection of ca. 0.47 ng herpes antigen/mL. Correlation of the expected dose with the actual dose gave a correlation coefficient of 0.98 (slope 0.969, intercept 5.07).

The present invention is particularly advantageous in that it is possible to provide sacs containing high concentrations of metals which are capable of forming complexes which are fluorescent. In addition, the use of such sacs provide for improved assays and in particular time delay fluorescent assays. Assays can be provided with improved sensitivities and/or shorter assay times.

These and other advantages should be apparent to those skilled in the art from the teachings herein.

Numerous modifications and variations of the present invention are possible in light of the above teachings; therefore, within the scope of the appended claims, the invention may be practiced otherwise than as particularly described.

What is claimed is:

1. A composition, comprising:
a mixture of an aqueous solution and a liposome, said liposome having encapsulated therein a solution of a detectable metal complexed with a chelating agent, said detectable metal being one which is fluorescent when complexed with an activator, said aqueous solution including a metal corresponding to the metal encapsulated within the liposome in a concentration sufficient to maintain a concentration of said metal encapsulated in the liposome of at least 5 millimolar.

2. The composition of claim 1 wherein the concentration is at least 10 millimolar.

3. The composition of claim 2 wherein the concentration is at least 15 millimolar.

4. The composition of claim 1 wherein the metal in the aqueous solution is in an unchelated form.

5. The composition of claim 4 wherein the metal is a rare earth metal.

6. The composition of claim 5 wherein the rare earth metal is europium.

7. The composition of claim 1 wherein the liposome is sensitized with a ligand selected from the group consisting of antigens, haptens and antibodies.

8. An assay for an analyte, comprising:
adding to a sample containing analyte the composition of claim 1;
releasing detectable metal from the liposome; and
determining a fluorescent signal from a fluorescent complex of the released detectable metal as a measure of analyte.

9. The assay of claim 8 wherein analyte is quantitatively measured.

10. The assay of claim 8 wherein fluorescent signal is determined by time delay fluorescence.

11. The assay of claim 8 wherein the liposome is sensitized with a ligand selected from the group consisting of antigens, haptens and antibodies.

12. The assay of claim 11 wherein the sample includes a binder for the analyte.

13. The assay of claim 12 wherein the concentration is at least 10 millimolar.

14. The assay of claim 12 wherein the concentration is at least 15 millimolar.

15. The assay of claim 8 wherein the metal in the aqueous solution is in an unchelated form.

16. The assay of claim 15 wherein the metal is a rare earth metal.

17. The assay of claim 16 wherein the rare earth metal is europium.

* * * * *